United States Patent [19]
Elsberry et al.

[11] Patent Number: 5,893,881
[45] Date of Patent: Apr. 13, 1999

[54] METHOD AND APPARATUS FOR ALLEVIATING CARDIOVERSION SHOCK PAIN BY DELIVERING A BOLUS OF ANALGESIC

[75] Inventors: Dennis D. Elsberry, New Hope; Rahul Mehra, Stillwater; Lynn M. Otten, Blaine; Mark T. Rise, Monticello; David L. Thompson, Fridley, all of Minn.

[73] Assignee: Medtronic, Inc., Minneapolis, Minn.

[21] Appl. No.: 08/920,645

[22] Filed: Aug. 29, 1997

Related U.S. Application Data

[63] Continuation of application No. 08/525,995, Sep. 8, 1995, Pat. No. 5,662,689.

[51] Int. Cl.$^6$ ............................................. A61N 1/39
[52] U.S. Cl. ............................................................ 607/5
[58] Field of Search ................................... 607/4, 5, 120

[56] References Cited

U.S. PATENT DOCUMENTS

| | | |
|---|---|---|
| 4,360,026 | 11/1982 | Venin et al. . |
| 5,087,243 | 2/1992 | Avitall . |
| 5,154,182 | 10/1992 | Moaddeb .......................... 607/120 |
| 5,203,326 | 4/1993 | Collins . |
| 5,220,917 | 6/1993 | Cammilli et al. . |
| 5,405,362 | 4/1995 | Kramer .................................. 607/5 |
| 5,562,708 | 10/1996 | Combs et al. ........................ 607/4 |
| 5,662,689 | 9/1997 | Elsberry et al. ...................... 607/5 |
| 5,727,556 | 3/1998 | Weth et al. . |
| 5,792,187 | 11/1998 | Adams ................................. 607/5 |

Primary Examiner—Marvin M. Lateef
Assistant Examiner—Carl H. Layno
Attorney, Agent, or Firm—Reed A. Duthler; Harold R. Patton

[57] ABSTRACT

An implantable cardioverter for providing cardioversion electrical energy to at least one chamber of a patient's heart in need of cardioversion and applying a pain alleviating therapy at an appropriate site in the patient's body prior to or in conjunction with the delivery of the cardioversion energy to the heart chamber to alleviate propagated pain perceived by the patient. The combined cardioversion and pain alleviating therapies are preferably realized in a single implantable, multiprogrammable medical device or separate implantable cardioversion and pain control devices with means for communicating operating and status commands between the devices through the patient's body.

15 Claims, 9 Drawing Sheets

5,893,881

METHOD AND APPARATUS FOR ALLEVIATING CARDIOVERSION SHOCK PAIN BY DELIVERING A BOLUS OF ANALGESIC

CROSS-REFERENCE TO RELATED APPLICATION

This application is a continuation of U.S. patent application Ser. No. 08/525,995, filed Sep. 8, 1995 and issued as U.S. Pat. No. 5,662,689 on Sep. 2, 1997.

FIELD OF THE INVENTION

The present invention generally relates to an implantable device for applying cardioverting electrical energy or shock to at least one chamber of a patient's heart in need of cardioversion preceded by the delivery of a pain suppression therapy to lessen the pain covered by the cardioversion shock.

BACKGROUND OF THE INVENTION

By way of definition, in the field of automatic implantable arrhythmia control devices, the term "cardioversion" or "cardioverter" refers to the process of and device for discharging relatively high energy electrical shocks or pulses into or across cardiac tissue to arrest a life threatening tachyarrhythmia. Cardioversion shocks or pulses may or may not be synchronized with a cardiac depolarization or rhythm and may be applied to arrest a malignant ventricular tachycardia or ventricular fibrillation with a selectable or programmable pulse energy. The arrest of atrial or ventricular fibrillation by such pulses is referred to as "defibrillation" (a form of cardioversion), and "defibrillators" have been characterized as a form of cardioverter. Products have been described and sold as combined, multiprogrammable, "pacemaker/cardioverter/defibrillator" systems for providing programmable staged therapies of anti-tachyarrhythmia pacing, synchronized cardioversion pulses and unsynchronized defibrillation pulses. In the following description and claims, it is to be assumed that the terms "cardioversion" and "defibrillation" are interchangeable, and that use of one term is inclusive of the other device or operation, unless specific distinctions are drawn between them in the context of the use.

Tachyarrhythmias are episodes of high rate cardiac depolarizations, typically occurring in one chamber of the heart but which may be propagated from one chamber to the other, that are sufficiently high in rate and chaotic that cardiac output from the chamber(s) is compromised, leading to loss of consciousness and death, in the case of ventricular fibrillation or weakness and dizziness in the case of atrial fibrillation or flutter and non-sinus atrial and ventricular tachycardias. Atrial fibrillation and flutter is debilitating but not life threatening unless it leads to ventricular fibrillation.

Fibrillation has generally been treated by means of high energy defibrillation shocks or pulses, which, in the context of implantable anti-arrhythmia devices, are applied by means of large surface area electrodes, including an electrode on or in the chamber to be defibrillated. The high energy level is employed in order to simultaneously depolarize the bulk of the heart chamber to be defibrillated, which will include tissues in all stages of the depolarization-repolarization cycle at the time the pulse is delivered.

Atrial fibrillation is probably the most common cardiac arrhythmia as reported in The Framingham Study reported in "Epidemiologic Features of Chronic Atrial Fibrillation", *THE NEW ENGLAND JOURNAL OF MEDICINE*, 306:17 1018–22, 1992, by W. Kannel, M.D. et al. Atrial fibrillation results in twice as many hospitalizations annually as bradycardia or ventricular tachyarrhythmia. The Framingham Study found an overall incidence of atrial fibrillation of approximately 0.1% per year among adults ages 25–64 years, and the prevalence in this population was approximately 2%.

Atrial fibrillation is associated with strokes thought to be caused by blood clots forming in areas of stagnant blood flow as a result of prolonging atrial fibrillation. In addition, patients afflicted with atrial fibrillation generally experience palpitations of the heart and may even experience dizziness or even loss of consciousness. Atrial fibrillation is otherwise not inherently life threatening if the ventricles are beating normally, but presumably may precipitate a life threatening ventricular tachyarrhythmia.

Atrial fibrillation occurs suddenly and many times can only be corrected by a discharge of electrical energy to the heart through the skin of the patient by way of an external defibrillator of the type well known in the art. Care must be taken in delivering the atrial cardioversion shock outside the vulnerable period of the ventricles. This treatment is commonly referred to as synchronized cardioversion and, as its name implies, involves applying electrical defibrillating energy to the heart in synchronism with a detected ventricular electrical activation (R-wave) of the heart outside of the vulnerable period. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Automatic implantable atrial defibrillators have been proposed to provide patients suffering from occurrence of atrial fibrillation with relief. For example, improved implantable atrial defibrillator and lead systems are described in the above-referenced '769 application and in commonly assigned U.S. Pat. Nos. 5,165,403, 5,292,338, and 5,314,430 incorporated herein by reference in their entireties. Delivery of an atrial defibrillation pulse at an inappropriate time in the cardiac cycle may induce ventricular arrhythmias, including ventricular fibrillation. An atrial sense amplifier and fibrillation detector is included in these systems to determine when the atria of the heart are in need of cardioversion, and a ventricular sense amplifier is included for sensing the R-waves. The atrial fibrillation detector causes a cardioverter stage to deliver defibrillating or cardioverting electrical energy to the atria in timed relation to a detected R-wave of the heart to avoid delivering the atrial cardioversion pulse into the vulnerable period of the ventricles.

In the system described in the '338 patent, for example, the output signal of the ventricular sense amplifier is also analyzed by a ventricular fibrillation detector to recognize ventricular fibrillation or other life threatening tachyarrhythmias. In the event that ventricular fibrillation or another life threatening ventricular arrhythmia is induced or occurs spontaneously, a ventricular cardioversion therapy is delivered to the ventricles. As a result, the atria can be automatically and safely cardioverted.

Unfortunately, the quantity of electrical energy which is required to cardiovert or defibrillate the atria is sufficient, in most cases, to cause a sudden, propagated pain in the patient's chest area or to stun the patient. Typically reported defibrillation thresholds between transvenous lead beating electrodes placed to provide atrial cardioversion pathways between the right atrium (RA) and coronary sinus (CS) or the superior vena cava (SVC) and CS are 1.3±0.4 J. Significant discomfort and often intolerable pain is associated with transvenous shock therapy in this range, resulting in the need for sedation of some patients and refusal to accept the therapy by other patients.

In addition, the successful cardioversion or defibrillation of the atria may also result in a rapid decrease in the patient's heart rate from a high and possibly variable heart rate. This rapid change in heart rate can, for some patients, cause discomfort or even temporary dizziness.

The atrial defibrillator and method of U.S. Pat. No. 5,332,400 provides a warning to the patient that an atrial cardioversion shock is about to be delivered in the form of electrical energy applied to internal tissue of the patient and being of a quantity so as to be discernable by the patient without pain or other undesirable effects. The warning also provides a sufficient time in advance of the delivery of the cardioverting shock to afford the patient with an opportunity to prepare for it. For example, if the patient is standing or walking and receives the warning, the patient may wish to find a place to sit in preparation. As another example, if the patient is driving an automobile and receives the warning, the patient may wish to safely pull off the road and park in preparation.

In summary, implantable atrial cardioverters capable of generating electrical energy of sufficient amplitude and duration delivered via either epicardial or endocardial electrodes have proven effective in converting atrial fibrillation or tachycardia to normal sinus rhythm. However, with delivered shock energy exceeding 1.0 joule, intractable pain occurs to the conscious patient which drastically limits the utility of this therapy, especially if atrial cardioversion is required several times a day.

Ventricular cardioversion shocks delivered by automatic implantable cardioverter/defibrillators are typically an order of magnitude greater in energy, in the range of 10.0–30.0 joules. However, the patient is usually unconscious by the time that the shock is delivered due to the loss of cardiac output. Nevertheless, patients report lingering chest muscle pain and discomfort from the successful cardioversion shock after awakening. Considerable research effort has gone into reducing the required ventricular cardioversion shock energy level in order to reduce the size and increase the longevity of the implanted device. To date, the reduced energy delivered is still great enough to result in considerable pain if the patient is still awake, and significant lingering pain exists following cardioversion shock energy delivery.

Turning to pain control through electrical stimulation, temporary or permanently implanted medical electrical nerve or spinal cord stimulation (SCS) devices for producing pain relief are widely available. The Medtronic® Itrel II implantable neurostimulation system is widely implanted for treatment and alleviation of intractable pain. Clinical reports and studies have shown that spinal cord stimulation, a.k.a. dorsal cord stimulation, appears to suppress angina pectoris pain symptoms. The effects of SCS on angina symptoms induced by pacing the subject's heart at an elevated rate been studied, as described, for example, in "Effects of spinal cord stimulation in angina pectoris induced by pacing and possible mechanism of action", BMJ, 307(21):477–450, Aug., 1993, by C. Mannheimer, MD, et al. Similar pain suppression effects have been reported in patients suffering exercise induced, or pain or fright response, angina symptoms in "Spinal cord stimulation in angina pectoris with normal coronary arteriograms", Coronary Artery Disease, 1993: 4:819–827 by T. Eliasson, MD, et al. It is postulated therein that spinal cord stimulation relieves pain by inhibiting impulse transmission in small fiber afferents by the activation of the large fiber afferents on the spinal segmental level.

Chronic angina symptoms arise at an exercise induced elevated heart rate when cardiac muscle is deprived of oxygen due to restricted arterial blood flow and lactate accumulates in the cardiac muscle deprived of oxygen. Typically, the patient reduces exercise level to lower the heart rate or is medicated. Acute angina symptoms arise in a "heart attack" when a restricted cardiac artery is blocked. Interventional therapies are required to restore the blood flow before the insufficiency results in myocardial ischemia. Neither chronic nor acute angina symptoms are necessarily related to an arrhythmia of a heart chamber which requires cardioversion and/or drug therapies to alleviate, and the SCS pain suppression described in these articles is not related to cardioversion.

Other approaches have also been proposed and nerve stimulation systems implanted in patients to control chronic angina and/or reduce a tachyarrhythmia heart rate to a normal rate. One such early implantable peripheral nerve stimulator, the Medtronic® Angistat carotid sinus nerve stimulator, operated by regulation of the patient's blood pressure through electrical stimulation of the carotid sinus nerve to initiate a reflex vagal activity which in turn effected a slowing in a patient's supraventricular tachycardia.

Electrical stimulation of the left or right vagus nerve to directly achieve this result was also implemented in the Medtronic® Barostat vagal nerve stimulator. In U.S. Pat. No. 5,330,515, a programmable, implantable vagal stimulator is described for stimulating afferent fibers for activating a descending anti-nociceptive pathway and thereby blocking incoming pain signals is described. A history of these stimulation systems and comparison to other pain control stimulation systems for various pain sources appears in the '515 patent.

The delivery of compensatory bradycardia pacing, if necessary to restore adequate cardia output, and other aspects of a combined nerve stimulator and pacemaker are described in U.S. Pat. No. 5,330,507. In U.S. Pat. No. 5,203,326, a combined antiarrhythmia pacemaker and nerve stimulator for stimulating selected autonomic nerves or ganglia in the patient's autonomic nervous system is also described. The above-referenced '278 patent application discloses a device which provides pulse bursts to the atrium, synchronized to detected atrial depolarizations, to stimulate the SA nodal fat pad and reduce the sinus rate of patients who suffer from angina. Systems of these types are not intended to cardiovert the heart nor do they have the effect of reducing pain attendant to the delivery of a defibrillation shock.

The alleviation of pain through the operation of implantable drug dispensers for automatically periodically delivering a bolus of a pain alleviating drug at a site in the body are also well known in the art. The Medtronic® SynchroMed" programmable implantable drug pump is implanted with a drug dispensing catheter for dispensing pain relieving or analgesic agent, e.g. analgesics, anesthetics, or spinal opiates, or for dispensing chemotherapy drugs or other agents to a specific body site. A combined catheter for delivering a pain relieving or analgesic agent and electrical lead for delivering electrical stimulation for treating various neurological disorders by simultaneous or sequential administration of either therapy is described, for example, in U.S. Pat. No. 5,119,832. Such a combined lead and drug dispensing catheter is currently employed in the Medtronic® Verify" temporary screening system for determining the most efficacious therapy at a given delivery site.

Returning to the treatment of atrial and ventricular tachyarrhythmias, a number of systems have been proposed to combine the delivery of an appropriate antiarrhythmic drug therapy as an alternative or companion therapy with the delivery of an appropriate cardioversion therapy as described, for example, in U.S. Pat. Nos. 4,987,897, 5,087, 243 and 5,269,301. In these systems, an implantable drug delivery system is combined with an implantable pacemaker/cardioverter/defibrillator, the system having a decision making control algorithm to govern the diagnosis of the arrhythmia, prioritize the therapies to be delivered, and deliver the therapies. It is hoped that the drug therapies can reduce the frequency of the need to deliver a defibrillation shock by either suppressing the tachyarrhythmia entirely or converting it to a lower rate or less chaotic tachyarrhythmia amenable to conversion by less aggressive high rate pacing therapies. In the event that a defibrillation shock is delivered to a conscious patient, the pain attendant to the shock is not alleviated by the delivered drug therapies. Nor does the delivery of an antiarrhythmic drug reduce the pain felt by the patient awakening from a ventricular defibrillation event.

Despite these notable improvements in implantable medical device technology, a need exists to reduce the pain and discomfort attendant to the intracardiac delivery of cardioversion shocks.

SUMMARY OF THE INVENTION

It is therefore an object of the present invention to alleviate the pain attendant to the delivery of a cardioversion shock to the atria or ventricles of a patient's heart.

The present invention therefore provides an implantable medical device and method of providing cardioversion electrical energy to at least one chamber of a patient's heart in need of cardioversion and applying a pain alleviating therapy at an appropriate site in the patient's body prior to or in conjunction with the delivery of the cardioversion energy to the heart chamber.

The present invention further provides a method of providing cardioversion electrical energy to at least one chamber of a patient's heart in need of cardioversion. The method and corresponding apparatus includes the steps of and means for detecting activity of the at least one chamber of the patient's heart, determining from the detected activity when the at least one chamber of the patient's heart is in need of cardioversion, applying a pain alleviating therapy to a site in the patient's body to alleviate the pain in body tissue arising from the delivery of the cardioversion energy, and applying the cardioversion energy to the at least one chamber of the patient's heart. Preferably, the application of the cardioversion energy to the at least one chamber of the patient's heart follows the delivery of the pain alleviating therapy by a time delay sufficient for the pain alleviating effect to take place.

The present invention is preferably realized in a method of and apparatus for providing atrial cardioversion shocks to the atria of a patient's heart in need of cardioversion wherein the application of the cardioversion shock to the atria follows thy delivery of the pain alleviating therapy by time sufficient to allow the therapy to take effect. Delivery of the atrial cardioversion shock is preferably synchronized with the detection of a ventricular depolarization with re-confirmation after the delay that atrial fibrillation is still present.

The patient is preferably warned of the imminent delivery of the cardioversion shock. In this regard, the delivery of spinal cord stimulation in itself provides a warning to the patient because it induces a perceptible parathesia that the patient may associate with the timing out of the delivery of the cardioversion therapy. An audio warning may also be provided with the delivery of the analgesic agent.

The pain alleviating therapy for the associated cardioversion energy induced and propagated pain is preferably either an analgesic drug or electrical neurostimulation to one or more specific sites of the peripheral and central pain pathways prior to administering therapeutic cardioversion energy. The combined cardioversion and pain alleviating therapies are preferably realized in a single implantable, multiprogrammable medical device or separate implantable cardioversion and pain control devices with means for communicating operating and status commands between the devices through the patient's body.

Advantageously, the propagated pain induced by the delivery of cardioversion energy may be reduced, particularly in atrial cardioversion, to a level allowing greater patient comfort and acceptance of the cardioversion therapy, particularly atrial cardioversion.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

Figure 1:
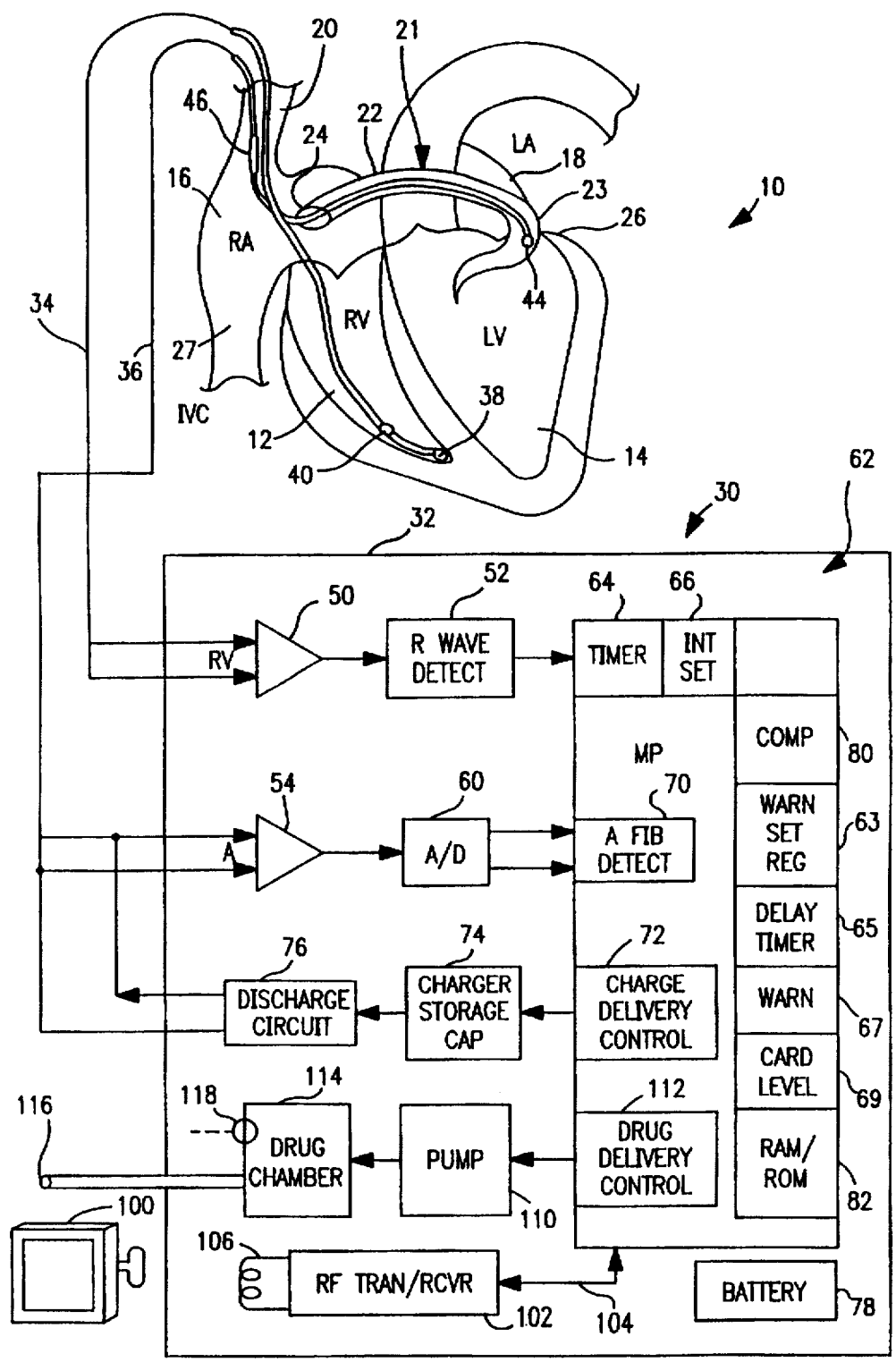
FIG. 1 is a schematic block diagram of a first embodiment of an automatic atrial cardioversion and pain alleviating system of the present invention employing the delivery of a pain alleviating drug therapy.
Figure 2:
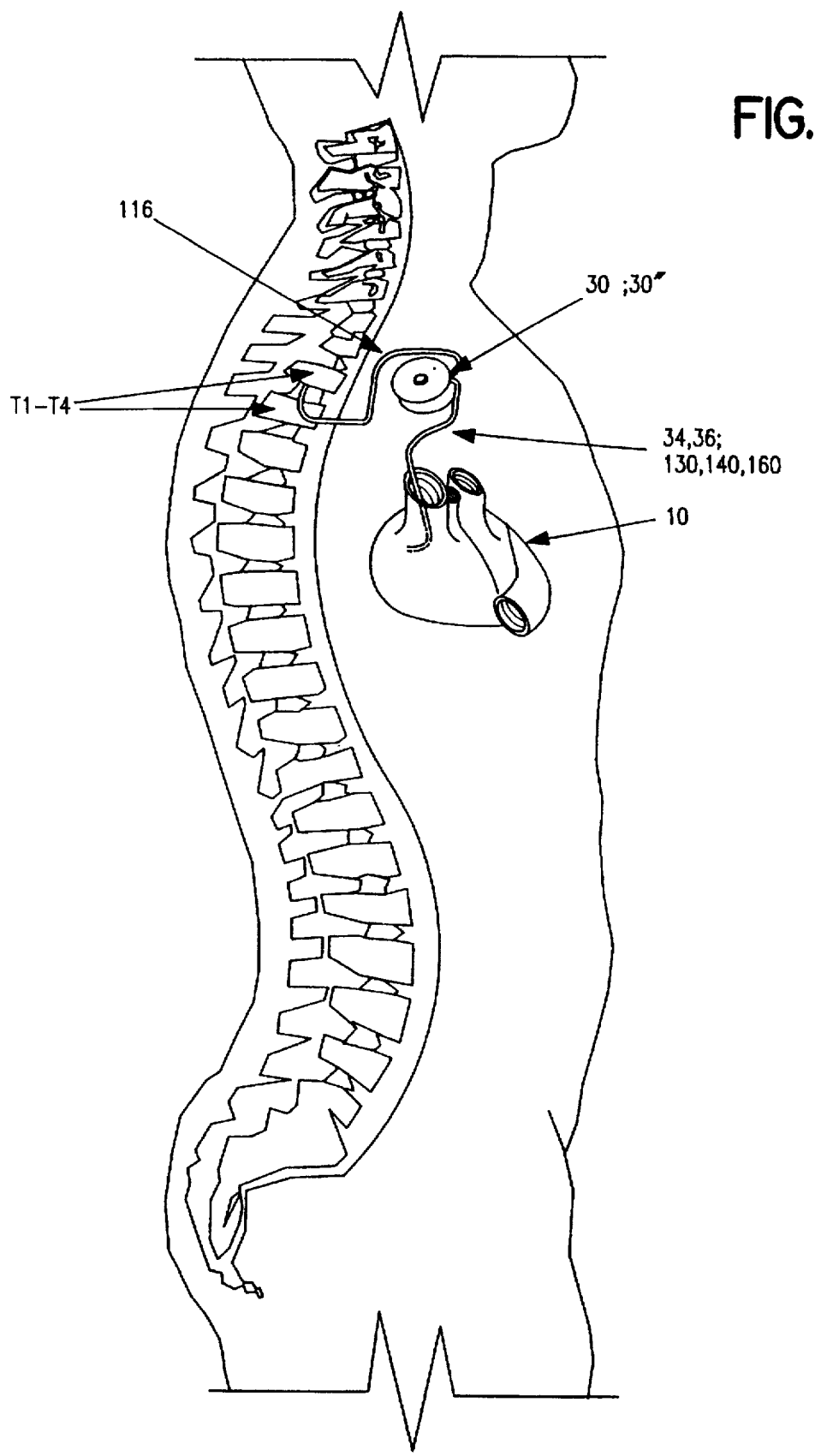
FIG. 2 is a schematic illustration of the system of the first embodiment implanted in a patient.

In a first embodiment of the invention, the therapeutic apparatus and implantation schema required for a totally integrated, permanently implanted, atrial cardioverter/drug delivery system 30 including a drug delivery catheter 116 and cardioversion lead system 34, 36 are illustrated in FIGS. 1 and 2. Associated with the delivery of cardioversion shocks to the heart 10, patients experience intractable pain from activation of nociceptors located within the intima of cardiac vessels with afferent fibers projecting via the sympathetics to T1–T4.

The infusion of various analgesic drugs or agents (or, simply "analgesics") including opiates (i.e. morphine sulfate, hydromorphone) and non-opiates (i.e. alpha-2 adrenergic agonists and neuron specific calcium channel blocking agents) have demonstrated rapid and effective analgesia following intrathecal administration to specific cord segments. As reported in the literature, the mechanism of action for these analgesics includes the blocking of projection from laminas I and II which receives input from myelinated Aδ and C nociceptors, respectively. Dependent upon the specific analgesic administered, it is also reported that the onset of pain suppression occurs in a few minutes to one hour, and the duration of analgesia may range from 4–24 hours. The delay in analgesia onset is not problematic, since rapid cardioversion is not necessary for atrial fibrillation as opposed to ventricular fibrillation. Time to analgesia can be utilized by the system 30 to re-verify the continuation of atrial fibrillation, charge storage capacitors to deliver the cardioversion shock, and ensure ventricular sensing to allow cardioversion shock synchronization with the R-wave of the cardiac cycle.

Referring now to FIG. 1, it illustrates a fully implantable atrial cardioverter/drug delivery system 30 embodying the present invention shown in association with a schematically illustrated human heart 10 in need of atrial fibrillation monitoring and potential cardioversion of the atria 16, 18 and an external programmer 100. The atrial cardioverter/drug delivery system 30 is capable of the sequential intrathecal delivery of a pain alleviating analgesic at therapeutic levels in the region of the T1–T4 segments of the spinal cord as shown in FIG. 2 followed by delivery of atrial cardioversion electrical energy pulses or shocks of sufficient amplitude and duration to effectively cardiovert the heart 10 in atrial fibrillation. The portions of the heart 10 illustrated in FIG. 1 are the right ventricle (RV) 12, the left ventricle 14, the right atrium (RA) 16, the left atrium 18, the SVC 20, the CS 21 including the CS ostium or opening 24, the left ventricular free wall 26 and the inferior vena cava 27.

The system 30 generally includes an enclosure 32, for hermetically sealing the internal circuit elements, battery, telemetry antenna, and a refillable drug reservoir or chamber, a bipolar RV lead 34, and a RA-CS lead 36. The enclosure 32 and leads 34 and 36 are arranged to be implanted beneath the skin of a patient so as to render the atrial cardioverter/drug delivery system 30 fully implantable.

The RV lead 34 preferably comprises an endocardial bipolar lead having electrodes 38 and 40 arranged for establishing electrical contact with the right ventricle 12 of the heart 10. The electrodes 38 and 40 permit bipolar sensing of ventricular depolarizations or R-waves in the right ventricle 12. As illustrated, the lead 34 is preferably fed through the SVC 20, the right atrium 16, and then into the right ventricle 12 to lodge the electrodes 38, 40 in the apex thereof as illustrated.

The RA-CS lead 36 generally includes a tip or CS cardioverting electrode 44 and a proximal ring or RA cardioverting electrode 46 as shown in the above-referenced '403 patent, for example. As illustrated, the RA-CS lead 36 is flexible and arranged to be passed down the superior vena cava 20, into the right atrium 16, into the coronary sinus ostium 24. The CS electrode 44 is advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the CS electrode 44 is positioned as described above, the RA electrode 46 is in the right atrium 16. The CS electrode 44 together with the RA electrode 46 provide bipolar sensing of heart activity in the atria 16 and 18.

The CS electrode 44 and the RA electrode 46 also provide for the delivery of defibrillating electrical energy to the atria. Because the CS electrode 44 is located beneath the left atrium 18 near the left ventricle 14 and the RA electrode 46 is within the right atrium 16, the cardioverting electrical energy, when applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of cardioversion electrical energy of the atria of the heart.

Further electrode systems and cardioversion pathways have been disclosed and are suitable for use in the practice of the present invention. One such atrial cardioversion electrode system is disclosed in the article "Safety and feasibility of transvenous cardioversion in atrial tachycardia", by Blanc et al., published in *Cardiac Pacing*, edited by Gomez, Future Pub. Co., 1985, pp 1526–1529. This electrode system employs a single lead with electrodes located in the right atrium and in the pulmonary artery. Delivery of atrial cardioversion shocks between an RV electrode and a subcutaneous electrode is disclosed in the above-referenced '338 patent. Delivery of atrial defibrillation pulses between a coronary sinus electrode and a subcutaneous electrode is also disclosed in the above-referenced '430 patent.

A further suitable atrial cardioversion electrode system is disclosed in the above-referenced '769 application. The electrode system disclosed therein includes an RA/SVC electrode (alone or optionally coupled to a subcutaneous electrode) and a CS electrode. The elongated RA/SVC electrode appears to provide atrial defibrillation thresholds in the range of about 1.0 Joule or less across a substantial portion of the patient population which represents a substantial improvement over the RA or SVC to CS/great vein electrode system employed in the above-referenced '403 patent.

Any of the above atrial cardioversion electrode systems and associated atrial and/or ventricular leads may be used in the practice of the present invention. However, even an approximately 1.0 joule cardioversion shock can be painful to a substantial portion of the population, particularly since atrial fibrillation episodes repeat frequently, requiring frequent cardioversion.

Within the enclosure 32, the system 30 includes a ventricular sense amplifier 50 coupled to the RV lead 34 to receive electrical signals in the ventricle across the bipolar electrode pair 38, 40 and an R-wave detector 52 to detect the R-waves therefrom. The ventricular sense amplifier 50 and the R-wave detector 52 form a first detecting means which senses R-waves in the electrogram transmitted to ventricular sense amplifier by the RV lead 34. The R-wave detector 52 is of the type well known in the art which provides an output pulse upon the occurrence of an R-wave being sensed during a cardiac cycle of the heart. The delivery of the atrial defibrillation shock or pulse is timed from the R-wave employing the ventricular timer 64 as described below.

The lead and electrode systems in certain embodiments of the above-referenced '338, '403 and '430 patents and the '769 patent application include an RV defibrillation electrode positioned on an RV lead inserted into the right ventricle and a pair of ventricular sense electrodes. Alternatively, in the atrial cardioversion system depicted in FIG. 1, common ventricular pacing leads having bipolar screw-in ventricular electrodes of this type may be employed as pace/sense electrodes 38, 40.

An atrial sense amplifier 54 is coupled to the RA-CS lead 36 to receive electrical signals or P-waves across the right atrium 16. The atrial sense amplifier 54 forms a second detecting means for detecting P-wave atrial activity of the heart picked up by the CS electrode 44 and RA electrode 46 of the RA-CS lead 36. The P-wave output signal of the atrial sense amplifier 54 is coupled to an analog to digital converter 60 which converts the analog signal representative of the atrial activity of the heart to digital samples for further processing to determine if atrial fibrillation is present and if the atrial cardioversion shock is effective in converting the atria to a normal atrial rate.

The enclosure 32 of the atrial cardioverter/drug delivery system 30 further include a microcomputer 62 that is preferably implemented in a manner disclosed in the above-referenced '338 patent and further as described hereinafter with respect to the flow diagrams of FIGS. 3 and 6. The implementation of the microcomputer 62 in accordance with this embodiment of the present invention results in a plurality of functional stages and RAM/ROM 82 for storing operating algorithms and programmable parameters as well as accumulated operating data for subsequent telemetry out to the external programmer 100.

The stages include the ventricular timer 64 for timing various intervals that recur in each QRST cycle as well as the R-wave synchronization time interval, an interval set stage 66 for selecting time intervals to be timed out in the ventricular timer 64, a delay timer 65 for timing out further delay times set in interval set stage 66 for the delivery of the pain alleviating therapy, an optional patient warning device 67 and warning set register 63, a cardioversion energy level set stage 69, an atrial fibrillation detector 70, a charge delivery control stage 72, an analgesic delivery control stage 112, and a computation stage 80.

The microcomputer 62 is arranged to operate in conjunction with RAM/ROM memory 82 which may be coupled to the microcomputer 62 by a multi-bit address bus and a bi-directional multiple-bit data bus. This permits the microcomputer 62 to address desired memory locations within the memory for executing write or read operations. During a write operation, the microcomputer 62 stores data, such as time intervals or operating parameters in the memory 82 at the addresses defined by multiple-bit data bus. During a read operation, the microcomputer 62 obtains data from the memory at the storage locations identified by the multiple-bit addresses provided over the address bus and receives the data from the memory 82 over the bi-directional data bus. Data related to the detections of atrial fibrillation and the deliveries of the therapies may be recorded in the RAM memory 82 for interrogation and telemetry out to the external programmer 100 in a manner well known in the art.

Detection of atrial fibrillation may be accomplished in atrial fibrillation detector 70, in conjunction with computation stage 80, of microcomputer 62 from the digitized P-waves detected by atrial sense amplifier 54 using any of the various atrial fibrillation detection methodologies known to the art. Generally, atrial fibrillation may be detected in response to an extended series of high rate (e.g. 240 b.p.m. or greater) atrial depolarizations or P-waves. If greater specificity for atrial fibrillation is desired, analysis of regularity of rate waveform morphology may also be employed.

Termination of atrial fibrillation may be detected in response to a decrease in the rate of atrial depolarizations and/or an increase in their regularity.

Appropriate detection methodologies are disclosed in the article "Automatic Tachycardia Recognition", by Arzbaecher et al., published in PACE, Vol. 7, May–June 1984, part II, pages 541–547 and in PCT Application No. US92/02829, Publication No. WO 92/18198 by Adams et al., both incorporated herein by reference in their entireties. In the PCT application, careful synchronization of the high voltage atrial defibrillation pulse to the ventricles to avoid induction of ventricular tachycardia or fibrillation is also discussed.

In addition, in the context of devices which automatically detect the occurrence of atrial fibrillation, the patient may optionally be warned of the detection of atrial fibrillation to be ready for the delivery of the atrial cardioversion shock through operation of the warning device 67. In this variation of this embodiment of the invention, a warning may be provided to the patient of the diagnosis of atrial fibrillation and the commencement of delivery of the pain alleviation drug therapy. The warning may be effected in the manner described in the above-referenced '400 patent, but is preferably effected by energizing a piezoelectric crystal oscillator that oscillates at an audible frequency intense enough for the patient to hear it and take precautions, if necessary. The patient may also optionally be provided with a limited function programmer 100 for use in communicating a command to the microcomputer 62 to prevent delivery of the cardioversion shock until the patient feels the effects of the pain alleviation therapy, at which time the patient may employ the programmer 100 to enable delivery of the cardioversion shock, subject to re-verification of the presence of the atrial fibrillation.

In this regard, the system 30 also includes the warning set register 63, the delay timer 65, and the warning device 67 that are utilized for generating the warning alarm for the patient when the atrial fibrillation detector 70 determines that the atria are in fibrillation. The warning device 67 may constitute an audible alarm sounding piezoelectric crystal oscillator for warning the patient that atrial fibrillation has been detected and that cardioverting electrical energy will be applied to the patient's atria.

If a programmer 100 is provided, it may also optionally include a patient activated command signal to initiate the delivery of the pain alleviating and cardioversion therapies in response to symptomatic atrial fibrillation. In this context as well, the ability to use the programmer 100 to delay the delivery of the cardioversion pulse until the patient has felt the effects of the pain alleviating therapy is believed valuable.

After the fibrillation detection warning is delivered to the patient, or after the patient requests cardioversion therapy by means of the programmer 100, register 63 is set to indicate that the patient has received the fibrillation detection warning or has requested therapy. Immediately thereafter, the delay timer 65 starts timing the warning delay period. The delay period defines a time interval from when the patient receives the warning or requests therapy to when the patient should first expect to receive the cardioverting electrical energy. The delay time is preferably programmable between one minute and twenty minutes to afford sufficient time to permit the pain alleviating therapy to take effect and for the patient to prepare for receiving the atrial cardioverting electrical energy. A second warning may optionally be given slightly before delivery of the cardioversion pulse, if desired. If the patient does not perceive the analgesic effect of the pain alleviating therapy during the warning delay, the patient may use the programmer 100 to reset the delay timer 65 to delay delivery of the cardioversion pulse until timer 65 expires. Alternatively, the programmer may instead allow the patient to delay delivery of the pulse until the patient perceives the analgesic effect, and allow delivery of the cardioversion therapy only following a patient initiated enable signal to the implanted device indicating that therapy may be delivered. As yet another alternative, the programmer may be employed to simply abort the therapy during the warning delay, which may be especially useful if therapy was initially requested by the patient, and the patient's symptoms have subsided.

A warning system as described above, including apparatus specifically dedicated to providing the warning may not be necessary if the patient can independently feel the analgesic take effect. As is noted below, the analgesia effect of intraspinal stimulation can be perceived almost immediately by the patient and effectively provides such a warning of impending delivery of a cardioversion shock.

Turning to the drug delivery system, it includes drug pump 110 which is operable to pump a programmed-in bolus of the pain alleviating drug from drug dispenser 114 through the drug delivery catheter 116 and into the region of spinal segments T1–T4 as shown in FIG. 2. The drug chamber 114 is percutaneously refillable through a septum 118. The drug delivery system components may take the form implemented in the Medtronic® SynchroMed" implantable drug dispenser. The drug infusing catheter 116 may be a Medtronic® Model 8700 series catheter. Timing of delivery and amount of drug delivered into the epidural space is programmed into the RAM/ROM 82.

Figure 3:
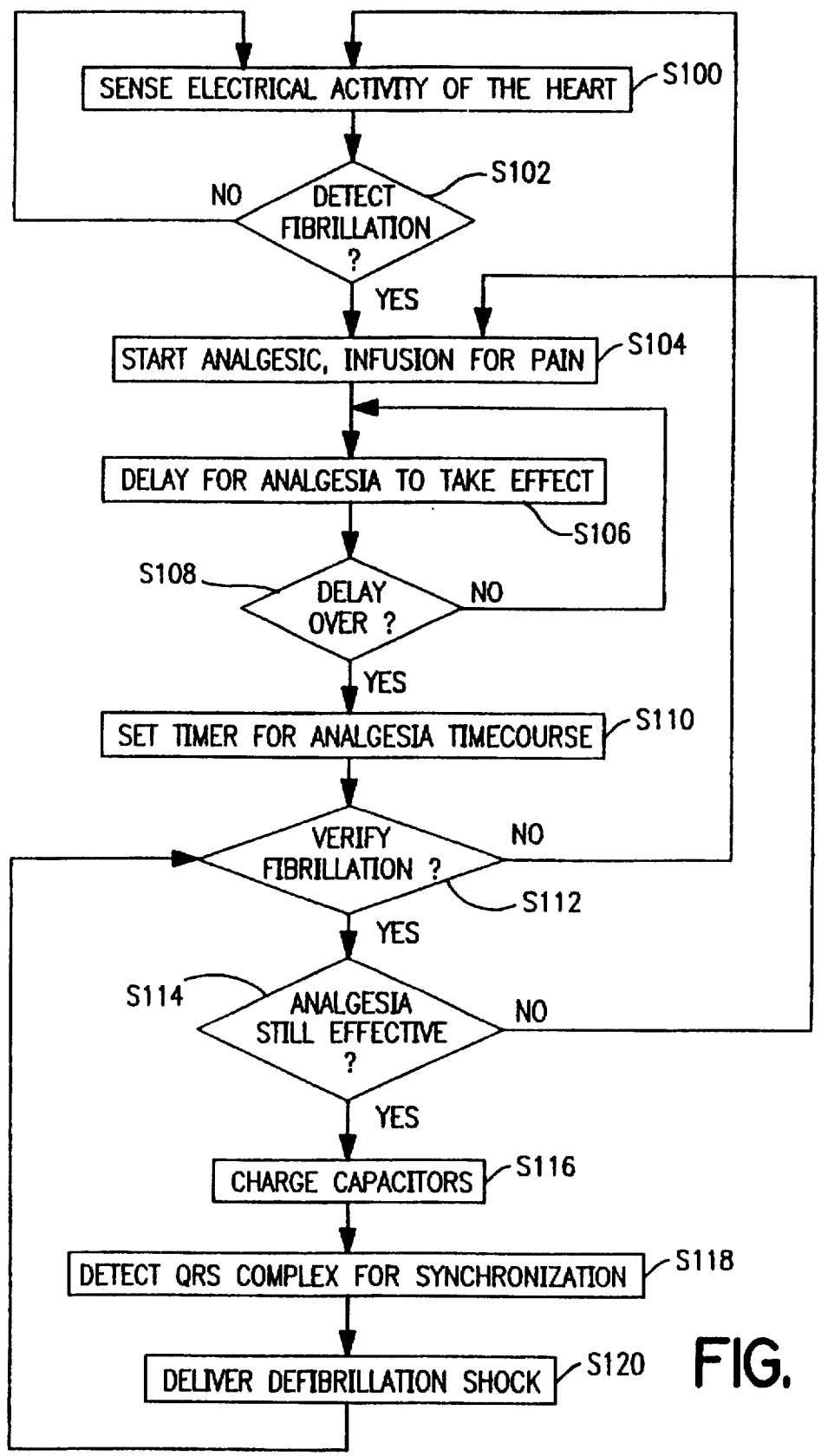
FIG. 3 is a flow chart of the operation of the system of FIGS. 1 and 2 in the alleviation of pain induced by delivery of an atrial cardioversion shock.

Turning now to FIG. 3, it depicts a flow chart of an operation of the microcomputer 62 in accordance with the first embodiment of the invention. At step S100, which continues at all times (except during the delivery of atrial cardioversion shock), atrial activity of the heart is sensed. At step S102, the atrial fibrillation detection algorithm is invoked in atrial fibrillation detector 72. If it is detected, then in step S104, the drug delivery control 72 operates drug pump 110 to pump a programmed-in bolus of the pain alleviating drug from drug dispenser 114 through the drug delivery catheter 116 and into the region of spinal segments T1–T4. The charge delivery control 72 may be commanded to start charge up of the charge storage capacitors, but it is preferred to delay capacitor charge up until the end of the delay for the analgesic to take effect and commence capacitor charge up during the analgesic time course, that is the time period that the analgesia effect is expected to continue. The optional warning steps are not included in the flow chart of FIG. 3.

The delay timer 65 is loaded and enabled to time out the delay for the analgesia effect to take place in steps S106 and S108. During this delay, the continuation of the atrial fibrillation episode may be verified in steps S100 and S102 and the algorithm may optionally be halted at that point. However, since atrial fibrillation bouts reoccur and since the bolus of pain alleviating drug is already delivered, re-confirmation at the end of the delay times is sufficient to determine whether or not to deliver the cardioversion shock therapy.

When the delay timer 65 times out in step S108, the delay timer 65 is reset for the analgesic time course and is started in step S100. The atrial fibrillation detection is re-verified in step S112 during the analgesic time course. If it only re-verified after the analgesic time course times out, then it is necessary to repeat steps S104–S114 until it is re-verified during an analgesic time course.

Then, in step S116, the charge delivery control 72 is commanded to enable the storage capacitor charge circuit 74 to charge the high voltage output capacitors up to the cardioversion energy set in level stage 69. The microcomputer 62 then sets a synchronization time interval in interval set stage 66 from an R-wave detected by R-wave detector 52. The ventricular timer 64 then provides a blanking signal to the ventricular and atrial sense amplifiers 50 and 54. Both operations may be performed in step S118. Re-verification of continued atrial fibrillation may also be performed between steps S116 and S118.

At the expiration of the synchronization time interval in ventricular timer 64, a command is applied through the charge delivery control 72 to operate the discharge circuit 76 to discharge the atrial cardioversion shock between the RA electrode 46 and the CS electrode 44 (or between any other suitable set of electrodes). After the atrial cardioversion shock is delivered, the atrial and ventricular sense amplifiers are again enabled, and the presence or absence of atrial fibrillation is again tested in step S112. If the episode is terminated, then the algorithm loops back to step S100.

If the episode is not terminated, the steps of FIG. 3 may be repeated, but at a higher programmed cardioversion energy level set in cardioversion level setting stage 69. After a certain number of attempts, the available therapies may be exhausted. Whether or not the therapies are successful, the patient will likely have been advised to contact the attending physician. The event history of the episodes and delivered therapies are recorded in RAM 82 for subsequent telemetry out and analysis by the physician in a manner well known in the art in order to assist in re-programming therapies.

Thus, the methodological sequence to provide the pain alleviating therapy to counter the pain induced by delivery of atrial cardioversion energy includes the initial detection of atrial fibrillation, optional warning to the patient, intraspinal drug infusion therapy to produce analgesia, time out to allow analgesia to take effect and the charge storage capacitors to be charged, re-verification of atrial fibrillation, delivery of the cardioversion energy, and verification that successful atrial defibrillation has taken place. Should successful atrial cardioversion not take place, the steps of FIG. 3 would be re-initiated, except that analgesic drug delivery would not be repeated unless the analgesic time course time had timed out in order to prevent drug overdose.

Depending on the analgesic employed, it may also be desirable to include a further timer to inhibit delivery of a further analgesic bolus timed from the previous delivery for a further time delay to prevent drug overdose. Such a timer may take into account the cumulative amount of analgesic delivered over a set time period.

In addition, it may be desirable to provide the patient with the option of using programmer 100 to temporarily program the delivery of an increased quantity of analgesic, if the desired analgesia effect is not achieved at the permanently programmed setting. A time and date record of such patient programmed increases may be kept in the system memory for review by the physician, and the repetitive use of the programmer may be inhibited.

A second embodiment of this atrial cardioversion and intraspinal pain alleviation therapy system is comprised of replacing the analgesic delivery component of the system with a spinal cord stimulator to present the alternate or additional intraspinal therapy of electrical stimulation in the region of spinal segments T1–T4 to effectively block pain transmission. SCS has been used in recent years for the treatment of severe angina pectoris refractory to conventional medical and surgical therapy in coronary artery disease as described above. Therapeutic analgesia from SCS is accomplished by the inserting a stimulation lead epidurally under local anesthesia at spinal segment level T7–T8 and advancing the lead's electrodes in the midline or a few millimeters left of midline to, typically, spinal segments T1–T2. Such a procedure is reported by Harke, J. et. al., "Spinal-cord stimulation (SCS) for pain relief from intractable angina-pectoris", *Anaesthetist* 42:557–563, 1993. However, actual electrode position may vary between spinal segments T1–T4 in order to achieve a distribution of parathesia matching the region of radiation of angina pain.

The stimulation pulse is approximately at 200 μsec, 80 Hz, at a voltage sufficient to produce the desired paraesthesia (typically 3.0V–6.0V). The analgesia produced is immediate, allowing the subsequent atrial cardioversion shock to be administered following re-verification of atrial fibrillation. A system and schema of this second alternative embodiment is presented in FIGS. 4 and 5, operating in accordance with the flow chart of FIG. 6. As an additional or alternative embodiment, neurostimulation pulses might also possibly be applied between electrodes in the vicinity of the heart, for example between defibrillation electrodes mounted on or in the heart and/or subcutaneous electrodes such as the housing of the cardioverter.

Figure 4:
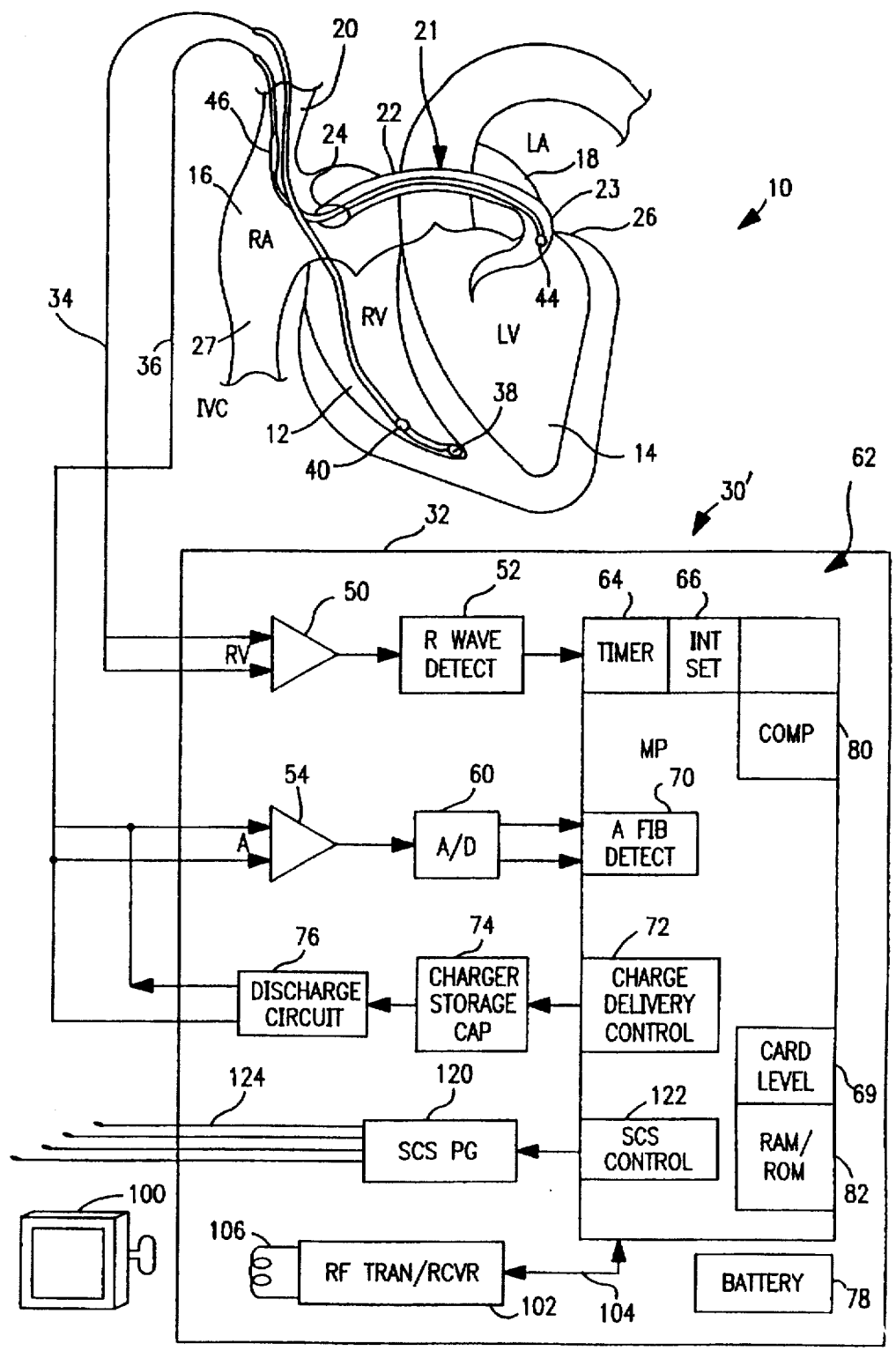
FIG. 4 is a schematic block diagram of a second embodiment of an automatic atrial cardioversion and pain alleviating system of the present invention employing the delivery of pain alleviating spinal cord stimulation therapy.
Figure 5:
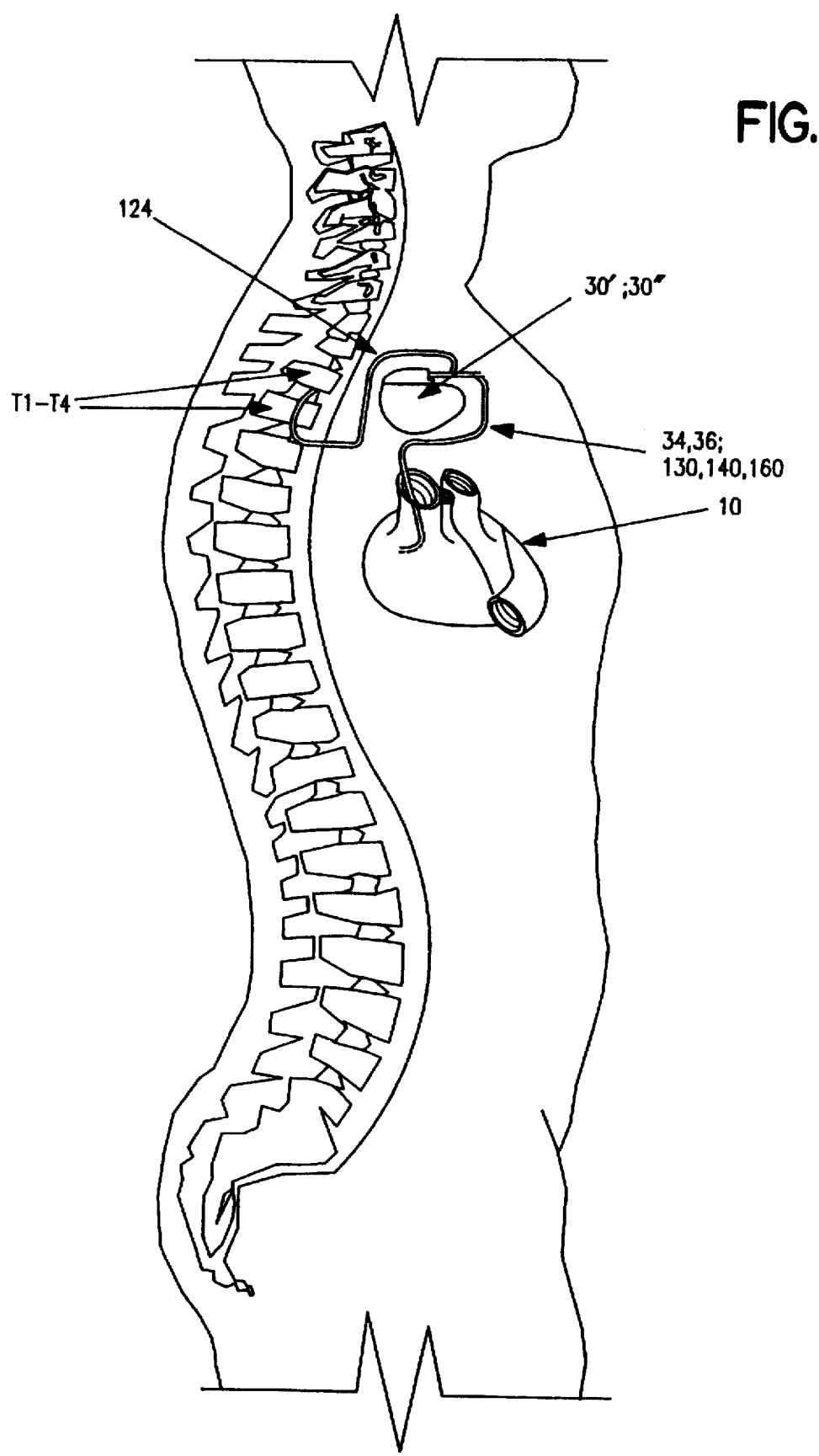
FIG. 5 is a schematic illustration of the system of the second embodiment implanted in a patient.

The atrial cardioverter/SCS delivery system 30' of FIG. 4 includes many of the same components as the system 30 of FIG. 1 with the substitution of the SCS components for the drug delivery components described above. Specifically, the SCS lead system 124 may be of the type described above and in the above-referenced '832 patent or in commonly assigned U.S. Pat. Nos. 5,255,691 or 5,360,441. These leads and the Medtronic® Model 3487A or 3888 leads include a plurality, e.g. four spaced apart distal electrodes that are adapted to be placed in the epidural space adjacent to spinal segments T1 and T2 as depicted in the schema of FIG. 5. The proximal end of the SCS lead system 124 is attached by a suitable connector block assembly to the SCS pulse generator 120 which is operated under the control of the SCS control stage of microcomputer 62.

The methodological sequence for dual neural or SCS stimulation and cardiac stimulation involves initial detection and verification of atrial fibrillation, epidural neural stimulation to produce paraesthesia, re-verification of atrial fibrillation, delivery of the atrial cardioversion shock, verification of successful atrial defibrillation, and cessation of the epidural neural stimulation. Should the atrial cardioversion shock prove unsuccessful, the process is repeated until the programmed-in cardioversion therapies prove successful or are exhausted. When successful defibrillation is confirmed, the epidural SCS stimulation is halted, and the system 30' reverts under the control of the algorithm of FIG. 6 to monitoring for the next atrial fibrillation episode.

Figure 6:
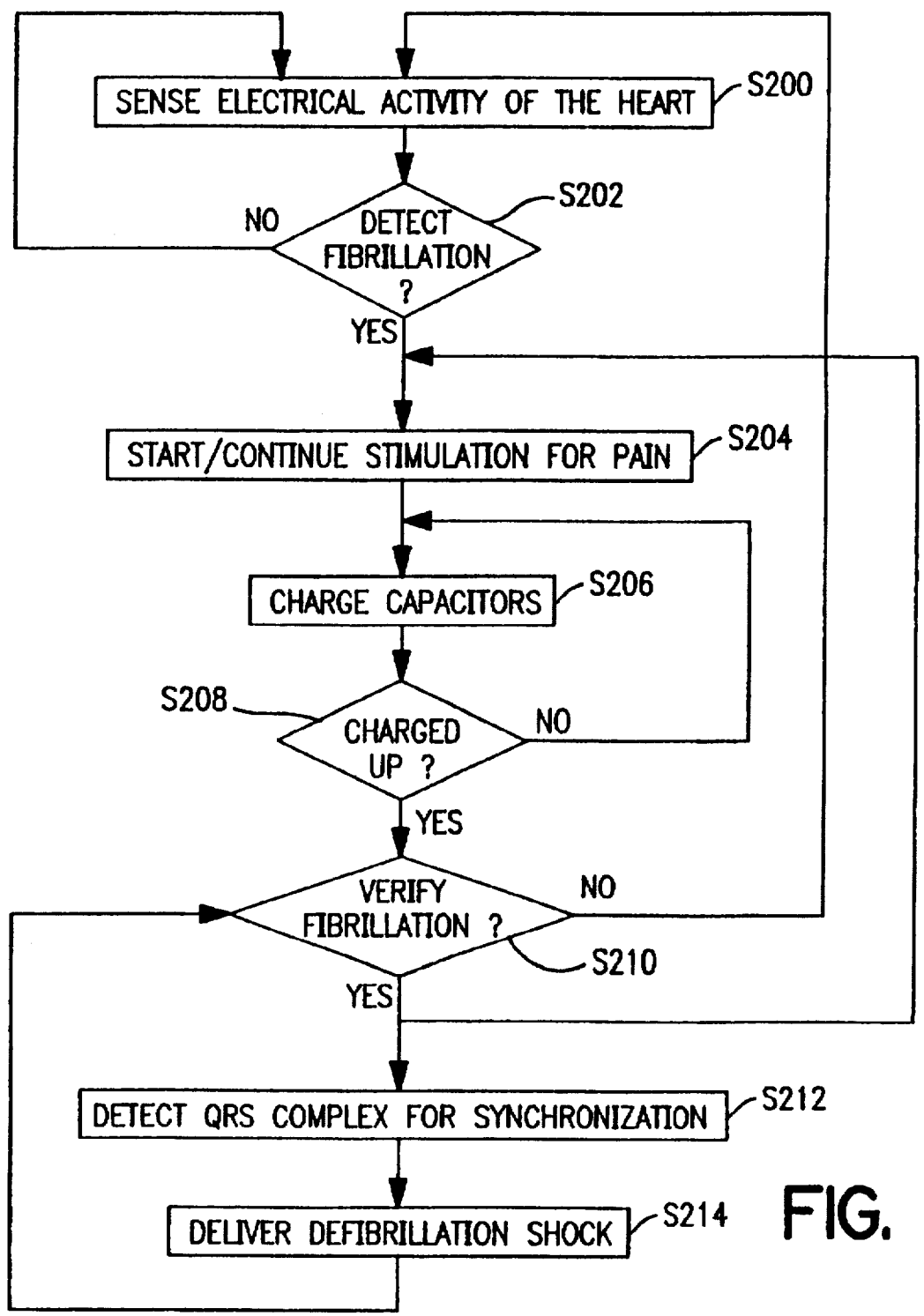
FIG. 6 is a flow chart of the operation of the system of FIGS. 4 and 5 in the alleviation of pain induced by delivery of an atrial cardioversion shock.

Thus, in FIG. 6, the steps S200–S214 parallel the steps S100–S120 of FIG. 3, except for the delay steps S106–S110. At step S200, which continues at all times (except during the delivery of atrial cardioversion shock), atrial activity of the heart is sensed. At step S202, the atrial fibrillation detection algorithm is invoked in atrial fibrillation detector 72. If it is detected, then in step S204, the SCS control 122 is commanded to operate the SCS pulse generator 120 at programmed-in parameter values stored in RAM/ROM 82 to deliver SCS pulses through lead 124 to the epidural space in the region of spinal segments T1–T2. The charge delivery control 72 may then be commanded in step S206 to start charge up of the charge storage capacitors 74.

After charge up is completed in step S208, the microcomputer 62 then sets a synchronization time interval in interval set stage 66 from an R-wave detected by R-wave detector 52. The ventricular timer 64 then provides a blanking signal to the ventricular and atrial sense amplifiers 50 and 54 and a command through the charge delivery control 72 to operate the discharge circuit 76 to discharge the atrial cardioversion shock between the RA electrode 46 and the CS electrode 44 (or between any other suitable set of electrodes). Both operations may be performed in step S212, after re-verification of continued atrial fibrillation in step S210. During re-verification of continued atrial fibrillation in step S210, delivery of neurostimulation pulses may be suspended to allow for optimal sensing of atrial electrical signals.

After the atrial cardioversion shock is delivered in step S214, the atrial and ventricular sense amplifiers are again enabled, and the presence or absence of atrial fibrillation is again tested in step S208. If the episode is terminated, then the algorithm loops back to step S200. If the episode is not terminated, the steps of FIG. 6 may be repeated, but at a higher programmed cardioversion energy level set in cardioversion level setting stage 69. After a certain number of attempts, the available therapies may be exhausted. Whether or not the therapies are successful, the patient will likely have been advised to contact the attending physician. The event history of the episodes and delivered therapies are recorded in RAM 82 for subsequent telemetry out and analysis by the physician in a manner well known in the art in order to assist in re-programming therapies.

As described above, the system of FIG. 4 is employed to deliver the intraspinal pain alleviation therapy of SCS with the stimulation electrodes placed as described above. The same pain alleviation therapy may be effected with electrodes placed in relation to afferent nerve fibers with appropriate programmed stimulation parameters and delivered in accordance with the flow chart of FIG. 6.

A third embodiment of the invention may employ the drug pump 110 for delivery of a sleep inducing agent such as a hypnotic, a barbitute, or a sedative as an alternative to or in conjunction with delivery of the pain alleviating therapies discussed above. As set forth in U.S. patent application Ser. No. 08/434,899, for an "Atrial Defibrillator and Method of use, filed May 3, 1995 by Bardy, an alternative method of reducing pain associated with atrial cardioversion is to deliver the cardioversion shock while the patient is asleep, and thus a sleep inducing agent may serve as a pain alleviating therapy.

In such an embodiment, it is presumed that delivery of the sleep inducing agent would be patient enabled by means of the programmer 100. For example, following detection of fibrillation by the implanted device and delivery of the fibrillation detection warning, or in conjunction with a patient request for cardioversion therapy, the patient may determine that delivery of a sleep inducing agent would be desirable. In such cases the sleep inducing agent may be delivered using the apparatus disclosed herein either alone or in conjunction with neurostimulation, and delivery of the cardioversion shock delayed for a time period sufficient for the patient to become unconscious. In a more complex embodiment, two separate drug pumps might be employed to allow delivery of the sleep inducing agent alone or in conjunction with an analgesic. The sleep inducing agent may be delivered systemically, by means of catheter 116, (FIG. 1) located in a peripheral blood vessel.

The detection warning, warning delay and the use of the programmer 100 to reset the delay timer 65 to delay delivery of a cardioversion pulse as discussed above in conjunction with the delivery of an analgesic apply as well to an embodiment in which the pain alleviating therapy includes delivery of a sleep inducing agent. In such case, expiration of the warning delay without resetting by the patient can be taken as evidence that the patient is asleep, allowing delivery of the drug. If the sleep inducing agent is not taking effect during the delay interval, the patient might either employ the programmer 100 to reset the warning delay or cancel therapy delivery.

A fourth embodiment of the invention may employ the drug pump 110 for delivery of a cardioversion or defibrillation threshold reducing agent such as D-salotol, Procainamide or Quinidine as an alternative to or in conjunction with delivery of the pain alleviating therapies discussed above. The reduction of defibrillation threshold in such case would provide the possibility of a reduced amplitude, less painful cardioversion pulse. The delivery of a threshold reducing agent thus can be employed as a pain alleviating therapy or as part of a pain alleviating therapy. In such case, the threshold reducing agent may be delivered using the apparatus disclosed herein either alone or in conjunction with neurostimulation. In a more complex embodiment, two separate drug pumps might be employed to allow delivery of the threshold reducing agent alone or in conjunction with an analgesic. The threshold reducing agent may be delivered systemically, by means of catheter 116, (FIG. 1) located in a peripheral blood vessel or the pericardial sac or may be retroperfused from the distal coronary sinus.

The detection warning and warning delay as discussed above in conjunction with the delivery of an analgesic apply as well to an embodiment in which the pain alleviating therapy includes delivery of a threshold reducing agent, to the extent that a delay is necessary in order to allow the threshold reducing agent to take effect prior to deliver of the cardioversion shock. The programmer 100 may still allow for the patient to cancel delivery of the cardioversion shock during the warning delay interval, but typically would not include the ability to reset the warning delay interval in the absence of a concurrently delivered analgesic. In such case, expiration of the warning delay can be taken as evidence that the threshold reducing agent has taken effect, will trigger delivery of a cardioversion shock provided the fibrillation persists. If an analgesic is delivered in conjunction with the threshold reducing agent, the ability of the patient to reset the delay interval until the analgesic effect is perceived would still be valuable.

Figure 7:
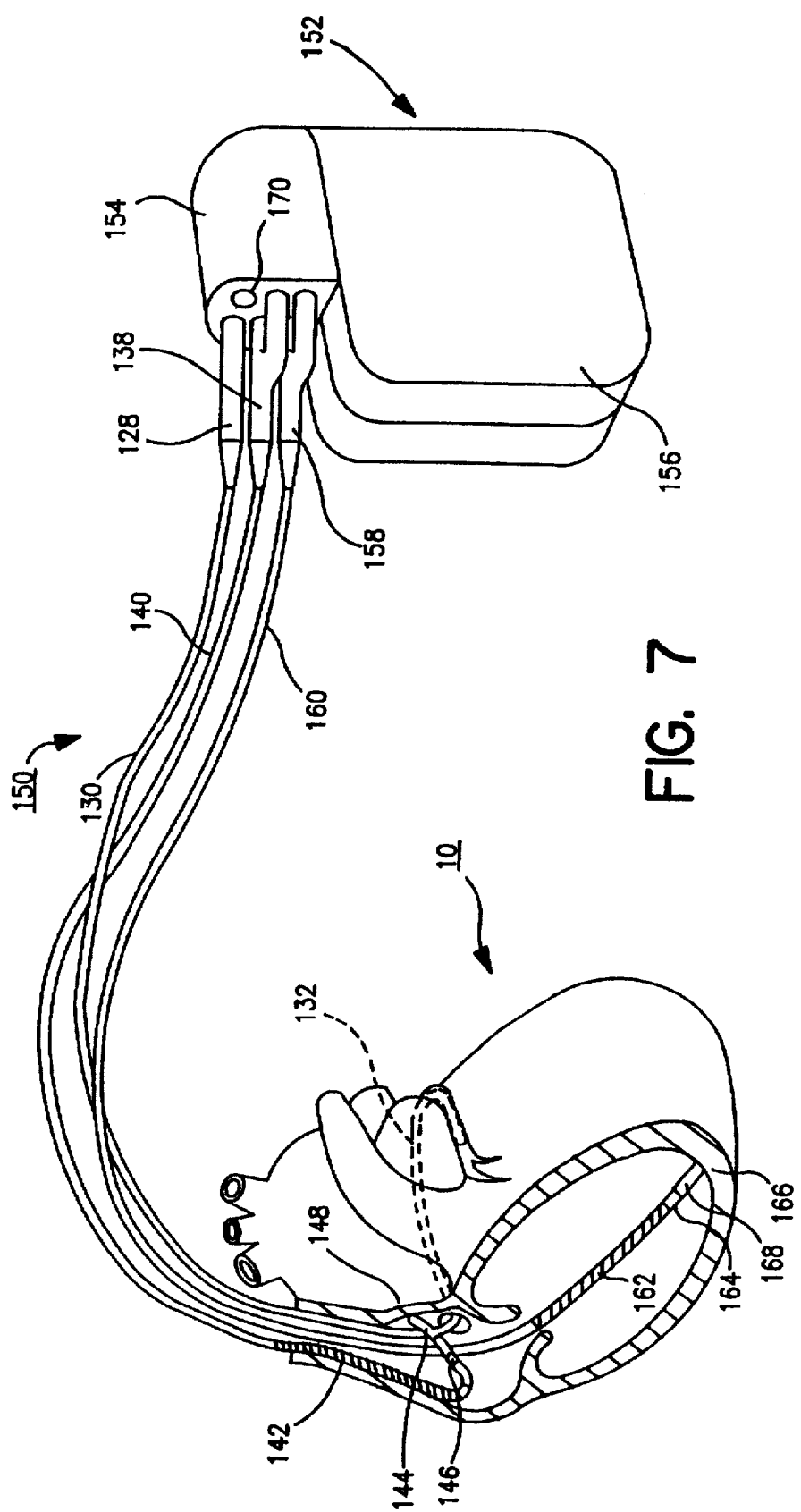
FIG. 7 is a modification of the systems of the first and second embodiments into a comprehensive pain alleviation fibrillation detection and cardioversion system.
Figure 8:
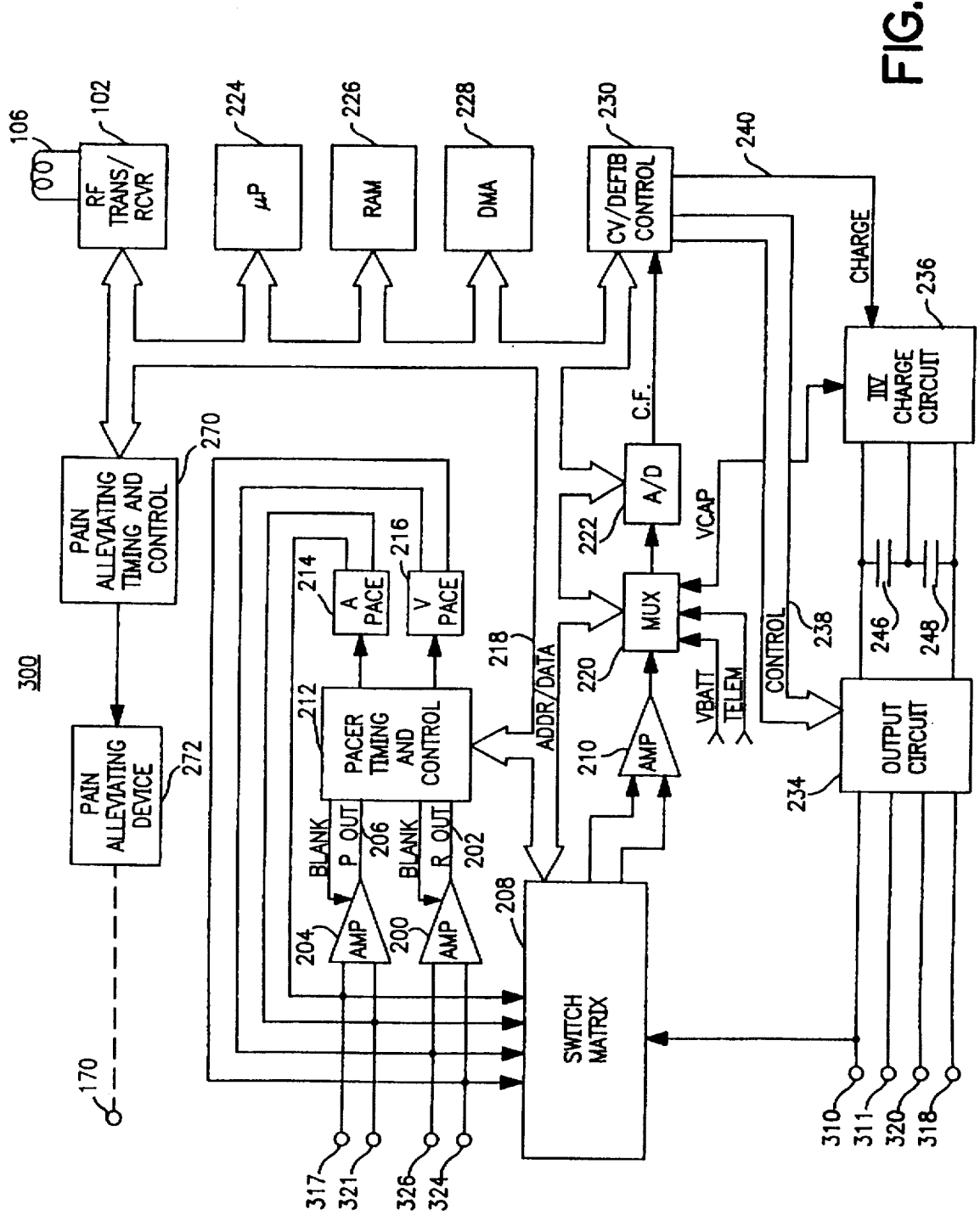
FIG. 8 is a schematic block diagram of an atrial and ventricular pacemaker/cardioverter/defibrillator and pain alleviation control circuit for use in the system of FIG. 7 for alleviating pain induced by the delivery of an atrial and/or ventricular cardioversion shock.

Turning now to a further aspect of the invention, the above-described embodiments may also be incorporated into an exemplary combined atrial and ventricular cardioversion and pain alleviation system wherein the components of a ventricular fibrillation detection and defibrillation system may be included in systems 30 or 30' to provide an extra margin of safety where there is a possibility that the delivery of atrial cardioversion energy may provoke ventricular fibrillation. FIGS. 7 and 8 illustrate a modification of the system of the first and second embodiments to incorporate ventricular defibrillation along with atrial cardioversion and the pain alleviation system of the present invention.

FIG. 7 schematically illustrates a pacemaker/cardioverter/defibrillator and intraspinal (or other site) pain alleviating system 150, including a pulse generator 152 (containing the comprehensive circuit 300 of FIG. 8) and a lead set, including a CS lead 130, an RA/SVC lead 140, and a ventricular lead 160. The system 150 also includes a pain alleviation electrical terminal and/or drug dispensing catheter port 170 for connection with an SCS stimulation lead 124 for providing epidural or other neural pain alleviating stimulation or an epidural drug dispensing catheter 116 for providing analgesics to the epidural space as described above, according to this further embodiment of the present invention.

The intraspinal version of pain alleviating system 150 may include the drug delivery components of the system 30 or the SCS or other neural stimulation components of system 30' or both. The pain alleviation components are described generally below in reference to the comprehensive circuit 300 of FIG. 8 as the pain alleviation timing and control circuit 270 and pain alleviating device 272. As described further below, the system of FIGS. 7 and 8 may be configured such that the pain alleviation timing and control circuit 270 and pain alleviating device 272 may comprise both forms of intraspinal analgesic and SCS pain alleviation therapies. The combined epidural catheter and nerve stimulation lead disclosed in the above-referenced '832 patent (incorporated herein by reference in its entirety) may be employed for the intraspinal delivery of both intraspinal analgesic and SCS pain alleviation therapies.

The ventricular lead 160 may take the form of the ventricular leads disclosed in the above-referenced '338 and '430 patents and includes three coaxial, coiled wire conductors separated from one another by tubular insulating sheaths. A ring electrode 164 and an extendable helix tip electrode 166, mounted retractably within an insulating electrode head 168, are located adjacent the distal end of the lead 160 and form a ventricular pace/sense, bipolar electrode pair. An elongated, exposed coil, cardioversion electrode 162 is located proximally to electrode head 168 and within the right ventricle. The RV electrode 162 may be fabricated from platinum, platinum alloy or other materials known to be usable in implantable defibrillation electrodes and may be about 5.0 cm in length. Electrodes 164 and 166' are employed for ventricular cardiac pacing and for sensing ventricular depolarizations or R-waves as described above. Each of the electrodes 162, 164, and 166 is coupled to one of the coiled conductors within the ventricular lead 160 which are coupled to three respective electrical connectors in a proximal end, bifurcated connector 158 which is in turn attached to receptacles in a connector block 154.

The RA/SVC lead 140 is constructed in a similar manner and includes a J-shaped distal end with a ring electrode 146 and an extendable helix electrode 148, mounted retractably within an insulating electrode head 144, forming an atrial pace/sense, bipolar electrode pair. Each of the electrodes 146 and 148 are coupled to one of the coiled conductors within the body of the RA/SVC lead 140 and are employed for atrial pacing and for sensing atrial depolarizations. An elongated, exposed coil atrial cardioversion electrode 142 is also provided, proximal to electrode 146 and coupled to the third conductor within the body of RA/SVC lead 144. Electrode 142 preferably may be about 10.0 cm in length or greater and is configured to extend from the SVC into the RA and toward the tricuspid valve. A bifurcated connector 138 which carries three electrical connectors, each coupled to one of the coiled conductors, is formed at the proximal end of the RA/SVC lead 140 for connection into receptacles of connector block 154.

The CS lead 130 takes the form of the coronary sinus lead disclosed in the above-referenced '430 patent, and includes a single coiled wire conductor, coupled to an elongated, exposed coil defibrillation electrode 132. Electrode 132, illustrated in broken outline, is located within the coronary sinus and great vein of the heart 10 and may be about 5.0 cm long. A connector 128 is coupled to the coiled conductor of the CS lead 130 and inserted into a further receptacle of the connector 154.

The system 150 includes the pulse generator 152 in combination with the leads, with the lead connector assemblies 128, 138, 158 inserted into the connector block 154. Optionally, insulation of the outward facing portion of the housing of the pulse generator 152 may be provided using a plastic coating, for example parylene or silicone rubber, as is currently employed in some unipolar cardiac pacemakers. However, the inward facing portion may instead be left uninsulated, or some other division between insulated and uninsulated portions may be employed, to be used as a subcutaneous cardioversion/defibrillation electrode alone or in combination with one or more of the lead bearing cardioversion/defibrillation electrodes to cardiovert or defibrillate either the atria or ventricles.

It should be noted that the leads and electrode systems as described to this point in regard to FIG. 7 are comprehensive of atrial and ventricular electrode systems and cardioversion/defibrillation pathways that may be combined or separated depending on whether atrial or ventricular cardioversion/defibrillation therapy is undertaken in conjunction with a pain alleviating therapy in accordance with the present invention. As noted in the above-referenced '769 application, the addition of the ventricular lead 160 and RV electrode 162 provides a further pathway for atrial defibrillation as well as a ventricular defibrillation pathway. In the former case, atrial cardioversion energy may be delivered between the RA/SVC electrode 142 (alone or optionally coupled with a subcutaneous electrode, e.g. pulse generator housing electrode 156) and the combination of the RV electrode 162 and the CS electrode 132. In the latter case, particularly efficient ventricular cardioversion/defibrillation may be effected in a pathway between the RV electrode 162 and a distributed electrode formed by electrically connecting the CS electrode 132 in common with the RA/SVC electrode 23.

FIG. 8 is a functional schematic block diagram of an implantable, comprehensive atrial and/or ventricular pacemaker/cardioverter/defibrillator and pain alleviating circuit 300 in which the present invention may usefully be practiced. This circuit diagram should be taken as exemplary of the type of system in which the invention may be embodied, and not as limiting, as it is believed that the invention may usefully be practiced in a wide variety of device implementations, including atrial and ventricular only cardioverter/defibrillators which may or may not provide anti-tachycardia and bradycardia pacing therapies.

With this understanding in mind, the most comprehensive circuit 300 of FIG. 8 will be described in conjunction with the lead-system of FIG. 7. The circuit 300 is provided with a terminals in the receptacles of connector block 154 for making electrical connection with the lead connectors 128, 138 and 158 and is also provided with the electrical terminal or catheter port 170 in connector block 154.

With respect to the terminals 310, 311, 318 and 320, terminal 310 is optionally coupled to the uninsulated housing electrode 156. Terminal 320 is attached to RV lead connector 158, and specifically makes connection with the RV electrode 162. Terminal 311 is adapted to make electrical connection with RA/SVC cardioversion electrode 142 through lead connector 138 and RA/SVC lead 140. Terminal 318 is adapted to make electrical connection with CS cardioversion electrode 132 through lead connector 128 and CS lead 130.

Terminals 310, 311, 318 and 320 are coupled to high voltage output circuit 234 which includes high voltage switches controlled by cardioversion/defibrillation control logic 230 via control bus 238. The switches within circuit 234 control which cardioversion electrode sets are employed and which are coupled to the positive and negative terminals of the high voltage output capacitor bank including capacitors 246 and 248 during delivery of the cardioversion shocks.

With respect to the terminals 317, 321, 324 and 326, terminals 324 and 326 are adapted to make electrical connection through connector 158 of RA lead 160 with the ventricular pace/sense electrode pair 164, 166. Terminals 324 and 326 are coupled to the R-wave sense amplifier 200, which preferably takes the form of an automatic gain controlled amplifier providing an adjustable sensing threshold as a function of the measured R-wave amplitude. A V-SENSE signal is generated on R-out line 202 whenever the signal sensed between electrodes 612 and 614 exceeds the present sensing threshold.

Terminals 317 and 321 are adapted to make electrical connection through connector 138 of RA/SVC lead 140 with the atrial pace/sense electrode pair 146, 148. Terminals 317 and 321 are coupled to the P-wave sense amplifier 204, which preferably also takes the form of an automatic gain controlled amplifier providing an adjustable sensing threshold as a function of the measured P-wave amplitude. An A-SENSE signal is generated on P-out line 206 whenever the signal sensed between terminals 317 and 321 exceeds the present sensing threshold.

Switch matrix 208 is used to select which of the available terminals are coupled to wide band (0.5–200 Hz) amplifier 210 for use in digital signal analysis. Selection of electrodes is controlled by the microprocessor 224 via data/address bus 218, which selections may be varied as programmed-in through RF transmitter receiver 102 and stored in RAM 226. Signals from the electrodes selected for coupling to bandpass amplifier 210 are provided to multiplexer 220, and thereafter converted to multi-bit digital signals by A/D converter 222, for storage in RAM 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The pacer timing/control circuit 212 includes programmable digital counters which control the basic time intervals associated with DDD, VVI, DVI, VDD, AAI, DDI and other modes of single and dual chamber pacing well known to the art. Circuit 212 also controls escape intervals associated with anti-tachyarrhythmia pacing in both the atrium and the ventricle, employing any anti-tachyarrhythmia pacing therapies known to the art.

Intervals defined by pacing circuit 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in RAM 226 and are communicated to the pacing circuit 212 via address/data bus 218. Pacer circuit 212 also determines the amplitude of the cardiac pacing pulses under control of microprocessor 224. During pacing, the escape interval counters within pacer timing/control circuit 212 are reset upon sensing of R-waves and P-waves as indicated by signals on lines 202 and 206, and in accordance with the selected mode of pacing on timeout trigger generation of pacing pulses by pacer output circuit 214 and 216, which are coupled to terminals 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, P-R intervals and R-P intervals, which measurements are stored in memory 226 and used to detect the presence of tachyarrhythmias.

Microprocessor 224 operates as an interrupt driven device, and is responsive to interrupts from pacer timing/control circuit 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or, intervals controlled by pacer timing/control circuit 212 take place following such interrupts.

For example, in response to a sensed or paced ventricular depolarization or R-wave, the intervals separating that R-wave from the immediately preceding R-wave, paced or sensed (R—R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P—P Interval) and the interval separating the sensed P-wave from the immediately preceding sensed or paced ventricular depolarization (R-P interval) may be stored. Preferably, a portion of the RAM 226 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R—R or P—P intervals of an average rate indicative of tachyarrhythmia or an unbroken series of short R—R or P—P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. Nos. 4,726,380, 4,880,005, and U.S. Pat. No. 4,830,006, all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated herein in its entirety. However, one of the advantages of the present invention is that it is believed practicable in conjunction with most prior art tachycardia detection algorithms.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuit 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuit 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuit 212. Following delivery of the fibrillation or tachycardia therapy the microprocessor then returns the device to cardiac pacing and awaits the next successive interrupt due to pacing or the occurrence of a sensed atrial or ventricular depolarization.

In the illustrated device, delivery of the atrial and/or ventricular cardioversion or defibrillation pulses is accomplished by output circuit 234, under control of control circuit 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuits for delivery of biphasic pulse regimens to multiple electrode systems may be found in the above U.S. Pat. Nos. 4,727,877 and 4,953,551 incorporated by reference in their entireties.

A specific switching circuit and explanation of the possible electrode combinations and benefits of such combinations is set forth in the above-referenced '769 application. For purposes of implementing the present invention, FIGS. 7 and 8 illustrate comprehensively the components that may be selectively employed in one variation to provide atrial cardioversion with ventricular cardioversion back-up if the atrial cardioversion energy were to induce ventricular fibrillation. In addition, the implementation of the present invention in a ventricular cardioverter/defibrillator is also possible through use of the components of the system of FIGS. 7 and 8.

In the event that atrial or ventricular fibrillation is identified, the typical therapy will be delivery of a high amplitude defibrillation pulse, typically in excess of 10.0 joules in the case of ventricular fibrillation and about 1.0 joule or less in the case of atrial defibrillation. Lower energy levels will be employed for synchronized cardioversion to convert a high rate tachycardia. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation.

Although the present invention has primary application to alleviating the pain attendant to atrial cardioversion, the above-described embodiments of the invention may have further utility in alleviating post-delivery pain felt by a patient on awakening after delivery of a ventricular cardioversion shock. In this regard, it will be understood that the pain alleviating components may be incorporated into a ventricular pacemaker/cardioverter/defibrillator of a type well known in the art not having the atrial cardioversion components and leads described above.

Returning to FIG. 8, the delivery of the pain alleviating therapy in anticipation of delivery of an atrial cardioversion shock therapy is accomplished by the microprocessor 224 operating the pain alleviation timing and control circuit 270. The pain alleviation timing and control circuit 270 is operable upon receiving the instruction from the microprocessor 224 to commence the pain alleviation therapy for the time period set in the instruction. In the case of atrial cardioversion and pain alleviating drug therapy, the flow chart of FIG. 3 may be followed. Similarly, the flow chart of FIG. 6 may be followed to control the timing and delivery of neural or SCS stimulation prior to and during delivery of the atrial cardioversion energy.

With respect to ventricular cardioversion/defibrillation, the ventricular shock must be delivered to the heart as soon as the output capacitors 246, 248 are charged to the programmed-in energy level and with or without synchronization to the R-wave. Consequently, there may not be time to deliver analgesic therapy and to wait for it to take affect. Therefore, the use of SCS or neural stimulation may be preferred for alleviating the pain and discomfort of ventricular cardioversion/defibrillation.

Alternative pain alleviation drug delivery therapies to those described above may include the intraatrial and/or intraventricular delivery of analgesics to counter the propagated pain attendant to the delivery of atrial cardioversion energy. The delivery of the analgesics directly into the atrium and/or ventricle may be effected through a lumen of the respective leads. Delivery of analgesics directly into the coronary sinus through a lumen of the RA-CS lead 36 could prove beneficial since the venous blood flow would be back toward the CS ostium 24 and right atrium at a relatively slow rate. Another alternative would be to deliver the analgesic bolus into the region of the nerve afferents from the heart which would provide coverage for all cardiac pain receptors.

One preferred alternative is to deliver the analgesic into the pericardial sac surrounding the epicardium so that the analgesia effect on cardiac muscle will be distributed about the heart. This alternative may be realized in the drug delivery embodiment of the dual chamber, multiprogrammable pacemaker/cardioverter/defibrillator system of FIGS. 7 and 8 or in the single chamber atrial cardioverter/ defibrillator system of FIGS. 1 and 3. In the former case, a drug delivery catheter may be attached to catheter port 170 and its distal end routed through the pericardial sac. In the latter case, the drug delivery catheter 116 from drug chamber 114 may be routed through the pericardial sac. Any of the cardioversion/defibrillation electrode systems described above may be employed in these systems.

Figure 9:
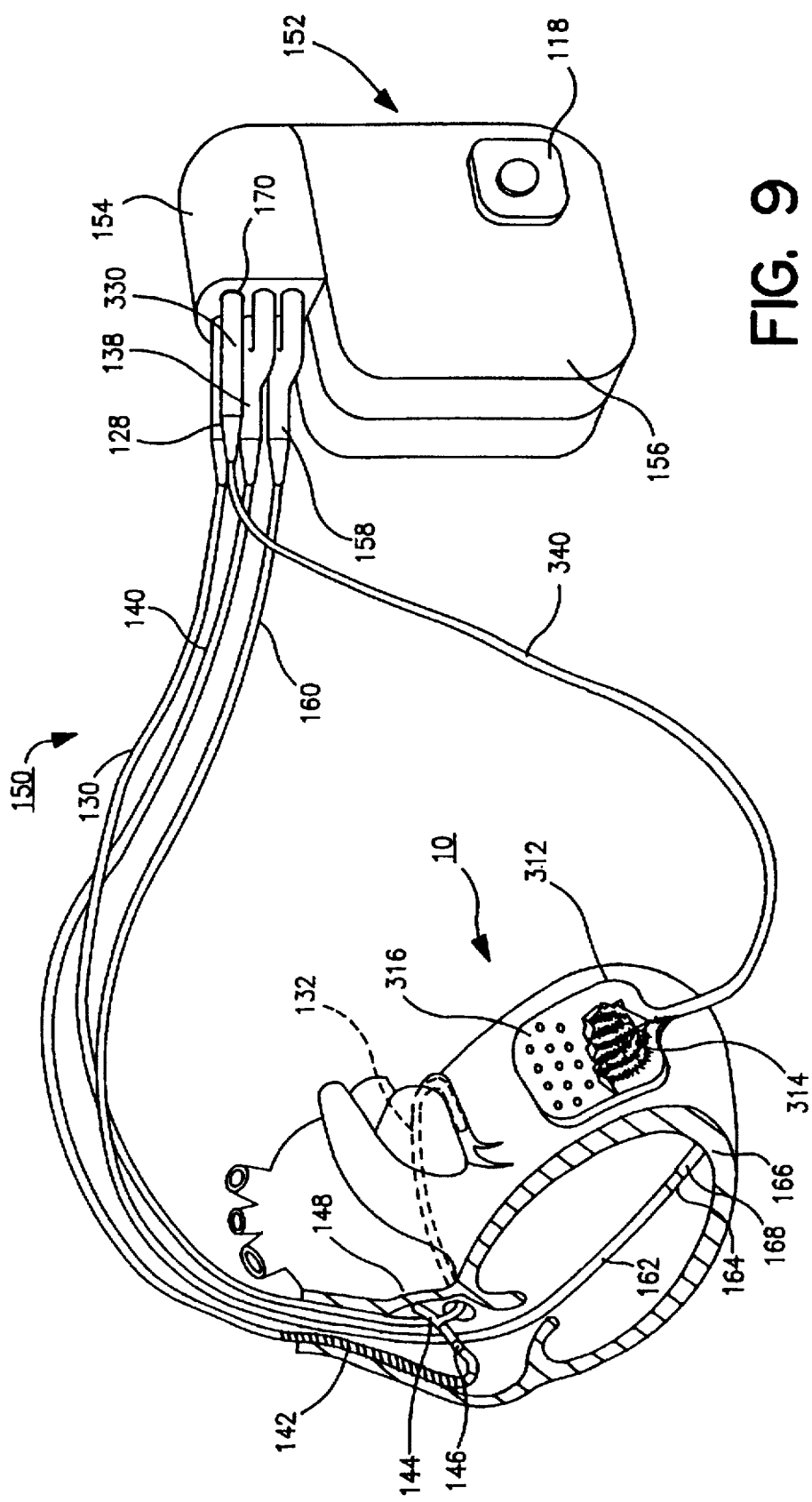
FIG. 9 is a further alternate embodiment of the system of FIGS. 1 or 7 for providing delivery of analgesic drugs directly to cardiac tissue.

In still another variation, the delivery of the analgesic may be effected through at least one combined epicardial drug delivery and defibrillation electrode patch 312 affixed to the epicardium of heart 10 through an opening in the pericardial sac as shown in FIG. 9. In this alternative, the electrode array 314 is substituted for the RV electrode 162 of FIG. 7 and is attached internally to one of the terminals 310 or 320 of FIG. 8 through catheter port 170. The combined pacemaker/ cardioverter/defibrillator and drug dispenser 152 includes an internal drug receiving chamber that is accessed for percutaneous refilling through a septum 118 and a drug pump as described above with respect to FIG. 1.

The patch 312 may be constructed with exposed electrically conductive cardioversion/defibrillation electrode 314 formed of mesh as described in the above-referenced '243 patent (incorporated herein by reference in its entirety) or formed with a distributed pattern of exposed coiled wire turns in a manner well known in the art. In either case, a chamber for receiving and distributing analgesic within the pericardial sac and over the epicardial surface of the heart 10 is formed within the insulating backing support pad 316 for the cardioversion/defibrillation electrode 314 in the manner described in the above-incorporated '243 patent. The backing support pad 316 has a permeable outer layer through which the analgesic permeates and is distributed. The analgesic may also be distributed through or alongside the cardioversion/defibrillation electrode 314. As illustrated in FIG. 9, the analgesic is dispensed by the internal drug pump through the port 170 and connector 330, a lumen of lead body 340, and an inlet into the interior chamber of the patch 312. Ventricular cardioversion/defibrillation energy may be delivered between the cardioversion/defibrillation electrode 314 and the SVC/RA electrode 142 and the CS electrode 132.

In a still further embodiment of the system of FIG. 9, the analgesic may be modified to allow it to be iontophoretically delivered into the myocardium by a low electrical energy applied to the electrode 314 in a manner described in the '243 patent. The iontophoretic delivery results in distributing the analgesic into the cardiac arterial system for circulation within the myocardium. In this embodiment, the system may include more than one cardioversion/ defibrillation electrode and drug delivery patch.

It should also be noted that in each of the above-described embodiments of FIGS. 1–8, the pain alleviating therapy components and the lead 124 and/or catheter 116 may be implemented into separate implantable medical devices that communicate with respect to the delivery of cardioversion therapies and pain alleviation therapies. It would be difficult at present to physically combine the drug chamber 114, septum 118, and drug pump 110 into a single housing for the system 30 or comprehensive circuit 300 with the components of an atrial cardioverter or an atrial-ventricular cardioverter or a pacemaker/cardioverter/defibrillator and also provide a suitable catheter port 170. It would be simpler to combine the SCS pulse generator 120 with the comprehensive circuit 300 of system 150, since additional space would only have to be provided for the additional electrical connector.

Consequently, the "Body Bus" system of the above-referenced '897 patent may be employed to communicate commands and status reports between a separately contained drug dispensing medical device or neural stimulation device and a pacemaker/cardioverter/defibrillator or a simpler cardioverter/defibrillator. In such a case, it would be expected that the dual chamber, multiprogrammable, pacemaker/cardioverter/defibrillator or the single chamber sub-system thereof would provide the operating commands to the separate drug dispensing or neural stimulation devices.

The external programmer 100 in all of the above described embodiments includes a telemetry transceiver and antenna for a two way telemetry link with the antenna 106 of RF transmitter/receiver 102. Operating modes and parameters may be programmed into or read out of RAM/ROM 82 through operation of the telemetry link in a manner well known in the art. In this manner, the drug dosage and time intervals or the SCS stimulation therapies described above may be programmed in. Data relating to the detection of atrial fibrillation episodes and the delivery of the drug therapy and cardioversion shocks may also be stored in RAM/ROM 82 for telemetry out on command of the external programmer 100 in a manner well known in the art.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. An implantable medical device system for delivering cardioversion energy to at least one chamber of a patient's heart in need of cardioversion and for alleviating pain attendant to delivery of cardioversion energy comprising:

detecting means for detecting activity of a chamber of the patient's heart;

determining means responsive to the detecting means for determining when the chamber of the patient's heart is in need of cardioversion;

cardioverting means responsive to the determining means for delivering cardioversion energy to the chamber of the patient's heart when the chamber is in need of cardioversion;

means for timing delivery of cardioversion energy from the application of the pain alleviating therapy to allow time dependent effects of the applied pain alleviating therapy to take effect; and means for delivering a bolus of an analgesic to the patient's body at an appropriate site in the patient's body to effect analgesia in conjunction with delivery of cardioversion energy to the heart chamber to reduce pain felt by the patient during delivery of the cardioversion energy.

2. The system of claim 1 wherein the pain alleviating therapy applying means comprises means for delivering the analgesic to the patient in the region of spinal segments T1 through T4.

3. The system of claim 1 wherein the pain alleviating therapy applying means comprises means for delivering neurostimulation pulses to the patient's nervous system to effect analgesia.

4. The system of claim 3 wherein the pain alleviating therapy applying means comprises means for delivering neurostimulation pulses to the patient in the region of spinal segments T1 through T4.

5. An implantable medical device system for delivering cardioversion energy to at least one chamber of a patient's heart in need of cardioversion and for alleviating pain attendant to delivery of cardioversion energy comprising:

detecting means for detecting activity of a chamber of the patient's heart; determining means responsive to the detecting means for determining when the chamber of the patient's heart is in need of cardioversion;

cardioverting means responsive to the determining means for delivering cardioversion energy to the chamber of the patient's heart when the chamber is in need of cardioversion; and means for applying a pain alleviating therapy at an appropriate site in the patient's body in conjunction with delivery of cardioversion energy to the heart chamber to reduce pain felt by the patient during delivery of the cardioversion energy; and wherein the pain alleviating therapy applying means comprises means for delivering a bolus of an analgesic to the patient's body to effect analgesia.

6. The system of claim 7 wherein the pain alleviating therapy applying means comprises means for delivering the analgesic to the patient in the region of spinal segments T1 through T4.

7. The system of claim 5 wherein the pain alleviating therapy applying means comprises means for delivering the analgesic to the patient's heart.

8. The system of claim 5 wherein:

said cardioverting means further comprises at least one cardioverting lead having a cardioverting electrode placed in contact with the patient's heart; and said pain alleviating therapy applying means comprises means for delivering the analgesic to the patient's heart through the cardioverting electrode.

9. The system of claim 5 wherein the pain alleviating therapy applying means further comprises means for delivering neurostimulation pulses to a pain pathway of the patient's nervous system to effect analgesia.

10. The system of claim 9 wherein the pain alleviating therapy applying means comprises means for delivering neurostimulation pulses to the patient in the region of spinal segments T1 through T4.

11. A method of delivering cardioversion energy to at least one chamber of a patient's heart in need of cardioversion comprising the steps of:

detecting activity of the at least one chamber of the patient's heart;

determining from the detected activity when the at least one chamber of the patient's heart is in need of cardioversion;

applying a pain alleviating therapy to a site in the patient's body to alleviate pain in body tissue arising from the delivery of the cardioversion energy; and delivering cardioversion energy to the at least one chamber of the patient's heart;

wherein the step of applying the pain alleviating therapy comprises delivering a bolus of analgesic to the patient's body to effect analgesia; and wherein the step of applying the pain alleviating therapy comprises delivering the analgesic to the patient in the region of spinal segments T1 through T4.

12. A method of delivering cardioversion energy to at least one chamber of a patient's heart in need of cardioversion comprising the steps of:

detecting activity of the at least one chamber of the patient's heart;

determining from the detected activity when the at least one chamber of the patient's heart is in need of cardioversion;

applying a pain alleviating therapy to a site in the patient's body to alleviate pain in body tissue arising from the delivery of the cardioversion energy; and delivering cardioversion energy to the at least one chamber of the patient's heart;

wherein the step of applying the pain alleviating therapy comprises delivering a bolus of analgesic to the patient's body to effect analgesia; and wherein the step of applying the pain alleviating therapy comprises delivering the analgesic to the patient's heart.

13. The method of claim 12 wherein:

the step of delivering cardioversion energy comprises placing at least one cardioverting lead having a cardioverting electrode in contact with the patient's heart; and wherein the step of applying the pain alleviating therapy comprises delivering the analgesic to the patient's heart through said cardioverting electrode.

14. A method of delivering cardioversion energy to at least one chamber of a patient's heart in need of cardioversion comprising the steps of:

detecting activity of the at least one chamber of the patient's heart;

determining from the detected activity when the at least one chamber of the patient's heart is in need of cardioversion;

applying a pain alleviating therapy to a site in the patient's body to alleviate pain in body tissue arising from the delivery of the cardioversion energy; and delivering cardioversion energy to the at least one chamber of the patient's heart;

wherein the step of applying the pain alleviating therapy comprises delivering a bolus of analgesic to the patient's body to effect analgesia; and wherein the step of applying a pain alleviating therapy further comprises delivering neurostimulation pulses to a pain pathway of the patient's nervous method to effect analgesia.

15. The method of claim 14 wherein the step of applying the pain alleviating therapy applying comprises delivering neurostimulation pulses to the patient in the region of spinal segments T1 through T4.

* * * * *